(12) United States Patent
Kim et al.

(10) Patent No.: US 11,185,314 B2
(45) Date of Patent: Nov. 30, 2021

(54) TEAR COLLECTION DEVICE

(71) Applicant: KOREA INSTITUTE OF SCIENCE AND TECHNOLOGY, Seoul (KR)

(72) Inventors: Jinseok Kim, Seoul (KR); Yong-Won Song, Seoul (KR); Jinwoo Jeong, Seoul (KR); Ockchul Kim, Seoul (KR); Won-suk Choi, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 1005 days.

(21) Appl. No.: 15/528,505

(22) PCT Filed: Oct. 19, 2015

(86) PCT No.: PCT/KR2015/011005
§ 371 (c)(1),
(2) Date: May 20, 2017

(87) PCT Pub. No.: WO2016/080658
PCT Pub. Date: May 26, 2016

(65) Prior Publication Data
US 2017/0252019 A1  Sep. 7, 2017

(30) Foreign Application Priority Data
Nov. 21, 2014  (KR) .......................... 10-2014-0163436

(51) Int. Cl.
*A61B 10/00* (2006.01)
*A61B 5/145* (2006.01)

(52) U.S. Cl.
CPC .......... *A61B 10/0045* (2013.01); *A61B 5/145* (2013.01); *A61B 5/14507* (2013.01); *A61B 2010/0067* (2013.01)

(58) Field of Classification Search
CPC . A61B 10/0045; A61B 5/145; A61B 5/14507; A61B 2010/0067; A61B 2560/0214; A61B 5/6821; A61B 5/15; A61B 10/02
See application file for complete search history.

(56) References Cited

U.S. PATENT DOCUMENTS 3,958,560 A * 5/1976 March ................ A61B 5/14555
600/319
4,635,488 A   1/1987 Kremer
4,640,594 A   2/1987 Berger
(Continued)

FOREIGN PATENT DOCUMENTS

CN   201108532 Y   9/2008
CN   102859358 A   1/2013
(Continued)

*Primary Examiner* — Rene T Towa
(74) *Attorney, Agent, or Firm* — Rabin & Berdo, P.C.

(57) ABSTRACT

A tear collection device comprises: a body attached to an eyeball; a tear inlet for allowing tear to flow into the body; a storing space formed inside the body and capable of storing the tears having flowed into the body; and a pump forming a pressure difference inside the body such that tears flow into the body through the tear inlet, wherein the pump is driven by using, as power, eye blinking movements of a wearer so as to form the pressure difference inside the body, thereby allowing the tears to flow into the body.

20 Claims, 10 Drawing Sheets

(56) References Cited

U.S. PATENT DOCUMENTS

| | | | |
|---|---|---|---|
| 5,919,356 A | 7/1999 | Hood | |
| 6,143,248 A * | 11/2000 | Kellogg | B01F 13/00 422/503 |
| 6,312,393 B1 | 11/2001 | Abreu | |
| 6,423,001 B1 | 7/2002 | Abreu | |
| 7,809,417 B2 | 10/2010 | Abreu | |
| 8,608,310 B2 | 12/2013 | Otis et al. | |
| 8,815,178 B2 * | 8/2014 | Bishop | A61B 5/14532 422/500 |
| 10,232,531 B1 * | 3/2019 | Etzkorn | B29C 43/18 |
| 2002/0049389 A1 * | 4/2002 | Abreu | A61B 5/14546 600/558 |
| 2003/0073932 A1 | 4/2003 | Varey | |
| 2004/0096959 A1 * | 5/2004 | Stiene | A61B 5/1473 435/287.2 |
| 2008/0065225 A1 * | 3/2008 | Wasielewski | A61B 5/14507 623/18.11 |
| 2010/0042209 A1 * | 2/2010 | Guarnieri | A61F 9/00781 623/4.1 |
| 2011/0028807 A1 | 2/2011 | Abreu | |
| 2014/0192315 A1 * | 7/2014 | Liu | A61B 5/14507 351/159.03 |
| 2014/0194706 A1 | 7/2014 | Liu et al. | |
| 2014/0277291 A1 | 9/2014 | Pugh et al. | |
| 2014/0309554 A1 | 10/2014 | Roy et al. | |
| 2014/0343387 A1 * | 11/2014 | Pugh | A61B 5/6821 600/365 |
| 2015/0063605 A1 * | 3/2015 | Pugh | A61B 5/6821 381/151 |

FOREIGN PATENT DOCUMENTS

| | | |
|---|---|---|
| CN | 103068308 A | 4/2013 |
| CN | 204293345 U | 4/2015 |
| DE | 10052879 A1 | 5/2002 |
| JP | 06-070933 A | 3/1994 |
| JP | 2014-530368 A | 11/2014 |
| KR | 10-2007-0006904 A | 1/2007 |
| KR | 10-2013-0116878 A | 10/2013 |
| WO | WO 2011/091473 A1 | 8/2011 |
| WO | WO 2012/009613 A1 | 1/2012 |
| WO | WO 2013-162756 A1 | 10/2013 |

* cited by examiner

TEAR COLLECTION DEVICE

TECHNICAL FIELD

This disclosure relates to a device for collecting tear, and more particularly, to a device for collecting tear, which may collect tear whose components are not diluted, without any artificial stimulation to the eyeball.

BACKGROUND ART

The tear includes inorganic electrolytes such as calcium and magnesium, and organic components such as glucose, lactic acid, protein, and lipid, so that the health condition may be measured by analyzing the concentration and composition of the tear.

In the past, artificial stimulation was applied to the eyeball to extract tear, and forced extraction of tear through a microtubule was used.

However, according to this existing method, components of the tear which serve as an indicator of various health conditions, including glucose, are diluted or fluctuated, so that tear components cannot be accurately analyzed.

DISCLOSURE

Technical Problem

This disclosure is directed to providing a device for collecting tear, which may naturally collect tear without any artificial stimulation since the device is directly worn on the eye to directly collect the tear discharged from the eye.

Technical Solution

In one general aspect, there is provided a device for collecting tear, comprising: a body placed over an eyeball; a tear inlet for allowing a tear to flow into the body; a storage formed inside the body and capable of storing the tear having flowed into the body; and a pump configured to form a pressure difference inside the body such that the tear flows into the body through the tear inlet, wherein the pump is driven by using an eye blinking movement of a wearer so as to form the pressure difference inside the body, thereby allowing the tear to flow into the body.

In an embodiment, the device for collecting tear may further comprise a tear outlet for allowing a tear to discharge from the body, and the tear may circulate by flowing into the body through the tear inlet from an outside of the body and then discharging out of the body through the tear outlet.

In an embodiment, the device for collecting tear may further comprise a micro-channel configured to extend into the body and communicate with the storage, and a net one-way valve may be formed at the micro-channel to prevent net reverse flow of the tear.

In an embodiment, the net one-way valve may be formed by changing a width of the micro-channel, and the width of the net one-way valve may be gradually increased along a flowing direction of the tear.

In an embodiment, a plurality of net one-way valves adjacently connected in series may be formed at the micro-channel.

In an embodiment, the body may be formed with a outer film and a inner film, the pump may include: a protrusion configured to convexly protrude from the outer film toward the outer of the body; and a chamber formed at the inner of the protrusion between the outer film and the inner film, the protrusion may be configured to be pressed due to a pressure of the eyelid when the wearer closes the eye and return to an original convex shape when the eye is opened, and the pressure difference may be generated by means of a pressure change inside the chamber, which is generated by outward and inward reciprocating movements of the protrusion when the wearer blinks the eye.

In an embodiment, the chamber may include: a pump entry through which the tear flows into the chamber; and a pump exit through which the tear discharges from the chamber, and a net one-way valve for preventing net reverse flow of the tear may be provided at the pump entry or the pump exit of the chamber, or at the pump entry and the pump exit of the chamber.

In an embodiment, the storage may include: a storage entry through which the tear flows into the storage; and a storage exit through which the tear discharges from the storage, and a net one-way valve for preventing net reverse flow of the tear may be provided at the storage entry or the storage exit of the storage, or at the storage entry and the storage exit of the storage.

In an embodiment, the device for collecting tear may further comprise a plurality of pumps, and the plurality of pumps may be arranged at an upstream side and a downstream side of the storage.

In an embodiment, the micro-channel may include a manifold, which is diverged into several branches, in a partial portion thereof, and one pump may be formed at each branch of the manifold.

In an embodiment, the body may be formed with a outer film and a inner film, the pump may include: the outer film convexly protruding toward the outer of the body; and a chamber formed between the outer film and the inner film, the outer film may be configured to be pressed due to a pressure of the eyelid when the wearer closes the eye and return to an original convex shape when the eye is opened, and the pressure difference may be generated by means of a pressure change inside the chamber, which is generated by outward and inward reciprocating movements of the outer film when the wearer blinks the eye.

In an embodiment, the chamber may form the storage.

In an embodiment, the tear inlet may be formed at a outer surface of the outer film.

In an embodiment, the device for collecting tear may further comprise a plurality of tear outlets configured to communicate with the inside of the body, and the plurality of tear outlets may be radially arranged at a side of the outer film.

In an embodiment, the device for collecting tear may further comprise a plurality of tear inlets and tear outlets, and the plurality of tear inlets and tear outlets may be radially formed in all directions of the body.

In an embodiment, the body may be in the form of a contact lens.

In an embodiment, the body may have a pupil region at a center thereof so that the pupil is located therein, and the storage may be formed away from the pupil region.

In an embodiment, the storage may be formed at a center portion of the body.

In an embodiment, the body may be formed with a outer film and a inner film, the storage may be formed in a space between the outer film and the inner film, and a pillar or an array of pillars may be formed at the storage to maintain the space between the outer film and the inner film.

In an embodiment, a sensor may be formed at the storage to detect components of the tear.

BEST MODE

Figure 1A:
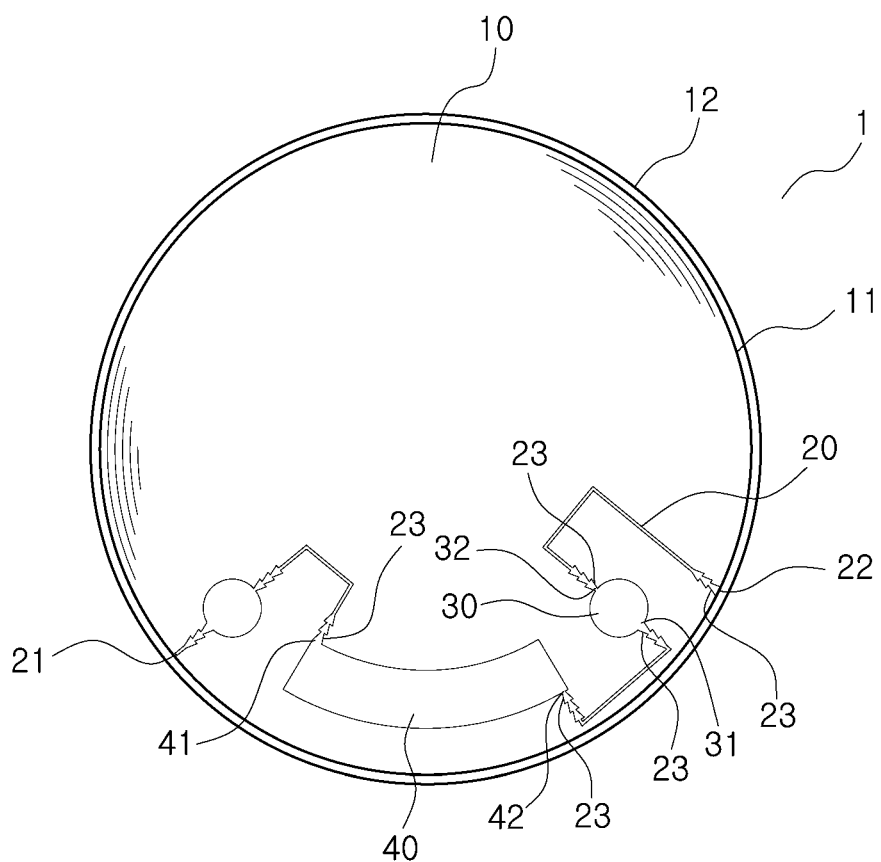
FIG. 1A and FIG. 1B show a device for collecting tear according to an embodiment of the present disclosure.

Hereinafter, an embodiment of the present disclosure will be described with reference to the drawings. Even though the present disclosure is described based on the embodiment depicted in the drawings, this is just an example, and the essential configuration and operations of the present disclosure are not limited thereto.

Figure 1B:
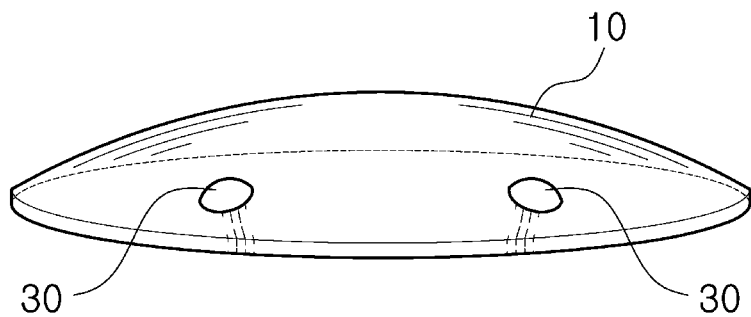
Figure 2:
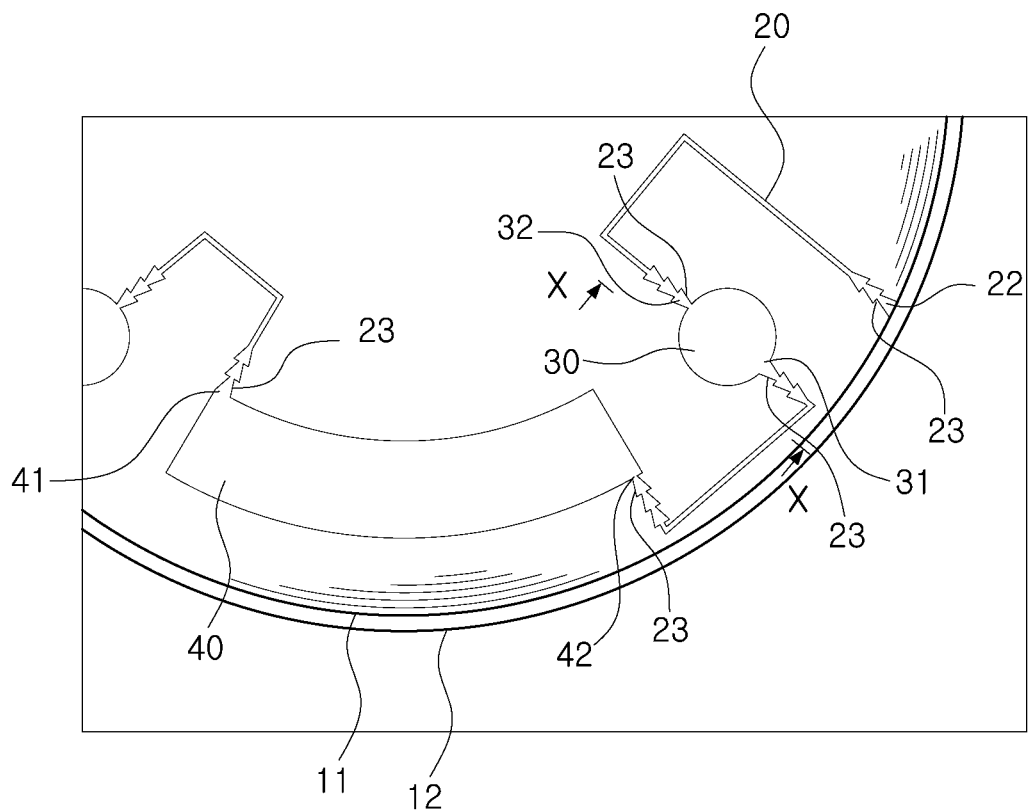
FIG. 2 is a partially enlarged view of FIG. 1A.

FIG. 1A and FIG. 1B show a device 1 for collecting tear according to an embodiment of the present disclosure. FIG. 1A shows the device 1 for collecting tear, observed at the outer, and FIG. 1B shows the device 1 for collecting tear, observed obliquely. FIG. 2 is a partially enlarged view of FIG. 1A.

As shown in FIGS. 1A, 1B and 2, a device 1 for collecting tear according to this embodiment includes a body 10 placed over an eyeball, a tear inlet 21 for allowing a tear to flow into the body, a storage 40 formed inside the body and capable of storing the tear having flowed into the body, and a tear outlet 22 for allowing a tear to discharge from the body.

In addition, the device 1 for collecting tear includes a micro-channel 20 configured to extend into the body 10, and a pump 30 configured to form a pressure difference inside the micro-channel 20 such that the tear flows through the micro-channel 20.

The tear inlet 21 and the tear outlet 22 communicate with each other through the micro-channel 20 extending into the body 10, and the storage 40 is formed on a path of the micro-channel 20.

The body 10 of this embodiment has a contact lens shape convex toward the outer, and a wearer may wear the device 1 for collecting tear simply by placing the device over the eyeball, such as by inserting a general contact lens.

The term "outer" used in the specification means an eyesight direction of the wearer when the wearer wears the body 10 of the contact lens on the eyeball, and the term "inner" means its opposite direction. Also, the term "lower" means a direction toward the ground, and the term "upper" means its opposite direction.

Figure 3:
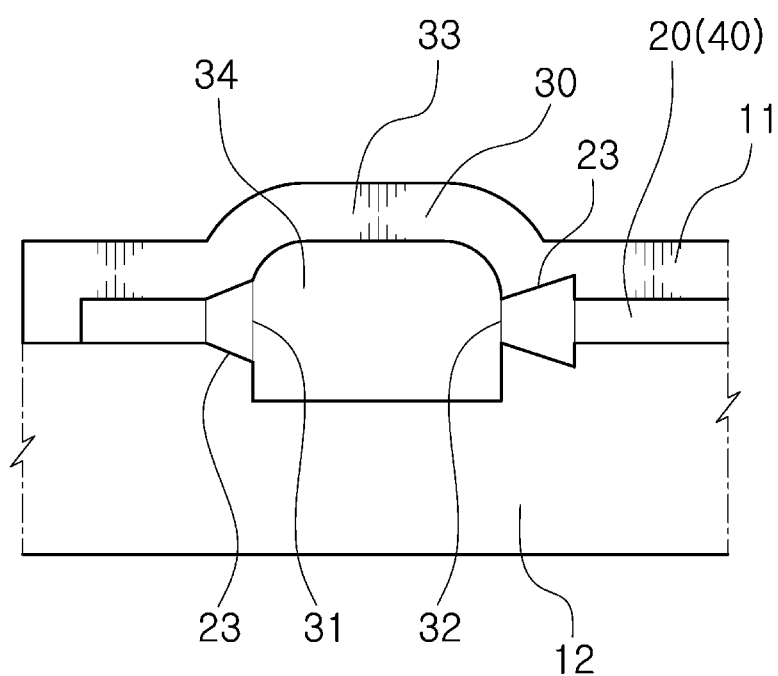
FIG. 3 is a side view, sectioned along the line X-X of FIG. 2.

FIG. 3 is a side view showing the device 1 for collecting tear, partially sectioned along the line X-X of FIG. 2. In FIG. 3, only a single net one-way valve 23 is depicted even though a plurality of net one-way valves can be connected in series.

The body 10 is formed by attaching two thin films, namely a outer film 11 and a inner film 12, to overlap each other.

According to this embodiment, the micro-channel 20, a chamber 34 of the pump 30, and the storage 40 are formed between the outer film 11 and the inner film 12, and as shown in FIG. 3, the micro-channel 20, the chamber 34 of the pump 30, and the storage 40 are formed through the inside of the body 10, except for a convex portion 33 of the pump 30 protruding outward from a outer surface of the outer film 11.

Referring to FIGS. 1A, 1B and 2 again, the micro-channel 20 serves as a tubular path through which the tear flows, and includes a tear inlet 21 for allowing a tear to flow in and a tear outlet 22 for allowing a tear to discharge from the micro-channel 20.

The tear discharged from the eye flows from the outside of the body 10 into the micro-channel 20 through the tear inlet 21, flows through the micro-channel 20, and flows out of the body 10 through the tear outlet 22. Hereinafter, the direction in which the tear flows from the tear inlet 21 to the tear outlet 22 is defined as "outward", and the opposite direction is defined as "reverse".

As shown in FIG. 3, on the path of the micro-channel 20, the storage 40 having a relatively larger cross-sectional area than the micro-channel 20 is formed.

The tear flowing through micro-channel 20 is stored in the storage 40. The device 1 for collecting tear may be removed from the eyeball and disassembled or compressed to collect the tear retained in the storage 40.

According to this embodiment, the tear flows in the micro-channel 20 due to the diffusion and coagulation of the fluid (the tear) caused by the pressure difference in the micro-channel 20.

The micro-channel 20 and the storage 40 may be filled with artificial tear so that the tear can be easily introduced into the narrow micro-channel 20 from the outside. In detail, before being worn by the wearer, the device 1 for collecting tear is immersed in a tank containing artificial tear for a long time so that the artificial tear is filled in the micro-channel 20 and the storage 40.

If a predetermined time passes in a state where the wearer wears the device 1 for collecting tear, the artificial tear stored in the storage 40 is entirely discharged out and replaced with natural tear discharged from the eye.

The pump 30 is provided to give power to allow a tear to flow into and through the micro-channel 20. The pump 30 is also formed on the path of the micro-channel 20, and one pump is arranged on each of both upstream and downstream sides of the storage 40 of this embodiment.

A net one-way valve 23 is formed at the micro-channel 20 to allow the tear to flow in the outward direction.

The net one-way valve 23 is formed by deforming the width of a portion of the micro-channel 20, and its width is gradually increased in the outward direction.

As the width is gradually increased in one direction, the tear flows smoothly in the direction in which the width is increased, but the tear does not smoothly flow in the opposite direction due to a kind of bottleneck phenomenon. Thus, the tear flows substantially more in one direction.

By adjusting an increase rate or the like of the width of the net one-way valve 23, the amount and speed of fluid flowing in the micro-channel may be adjusted.

The net one-way valve 23 is also disposed at a pump entry 31 and/or a pump exit 32 of the pump 30 as well as at a storage entry 41 and/or a storage exit 42 of the storage 40. In addition, the net one-way valve 23 is also formed in the vicinity of the tear inlet 21 and the tear outlet 22.

As shown in FIG. 2 in a best way, according to this embodiment, a plurality of net one-way valves 23 may be adjacently connected to each other in series, which may more effectively prevent the tear from flowing in the reverse direction.

Figure 4A:
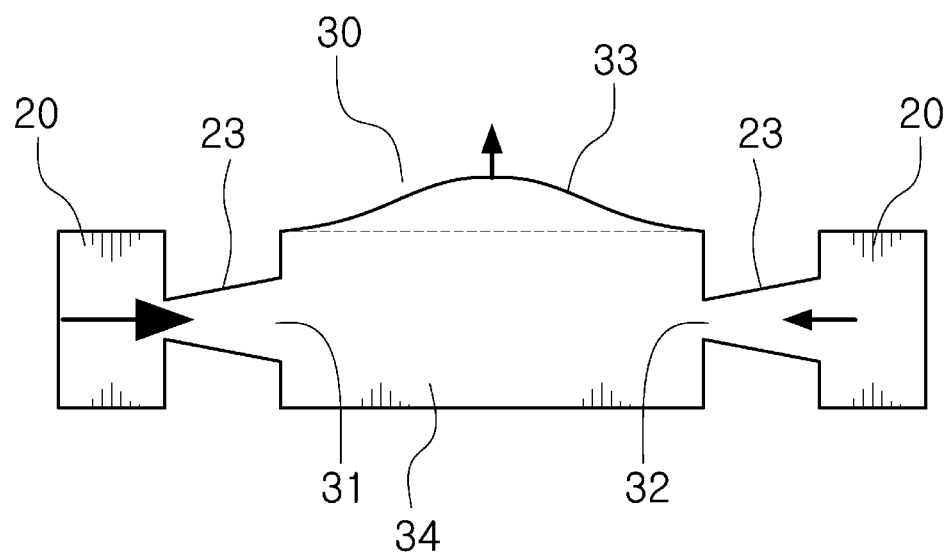
FIG. 4A and FIG. 4B show that tear flows by means of an operation of a pump according to an embodiment of the present disclosure.
Figure 4B:
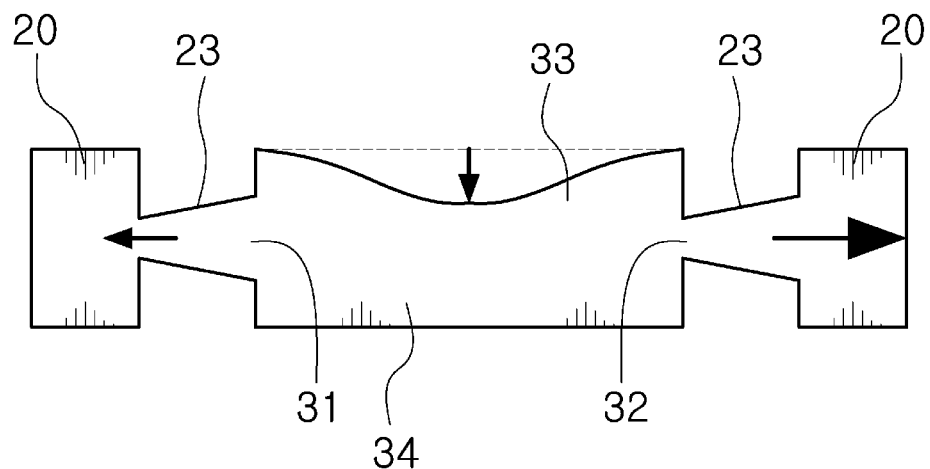

FIG. 4A and FIG. 4B show that tear flows by means of an operation of a pump 30 according to an embodiment of the present disclosure.

As shown in FIG. 4A and FIG. 4B, the pump 30 includes a protrusion 33 convexly protruding outward and a chamber 34 formed at the inner side of the protrusion 33 and communicating with the micro-channel 20.

Referring to FIG. 3 again, the protrusion 33 of the pump 30 is formed in a shape in which the outer film 11 of the body 10 protrudes partially and is formed integrally with the body 10.

Since the protrusion 33 protrudes on outer surface of the body 10, when the wearer closes the eye, the protrusion 33 is pressed downward due to a pressure and shear force of the eyelid. Also, the protrusion 33 has elasticity so that when the wearer opens the eye, the protrusion 33 returns to an original convex shape.

The chamber 34 is formed on the path of the micro-channel 20 and includes a pump entry 31 through which the tear flows into the chamber 34 from the micro-channel 20 and a pump exit 32 through which the tear flows out of the chamber 34 into the micro-channel 20.

As shown in FIG. 4B, when the wearer closes the eye, the protrusion 33 is pressed inward (downward in the drawing), and the pressure of the pump entry 31 and the pump exit 32 rises.

At this time, the net one-way valve 23 of the pump inlet 31 has a sectional area gradually decreased in the reverse direction (in a left direction on the figure), and the net one-way valve 23 of the pump exit 32 has a sectional area gradually increased in the outward direction (in a right direction on the figure). Thus, the tear in the chamber 34 moves in the outward direction in which the pressure is substantially relatively lowered, and the movement in the reverse direction is reduced. Thus, the tear flows in a direction in which the tear exits the chamber 34 through the pump exit 32.

On the contrary, as shown in FIG. 4A, when the wearer opens the eye, the protrusion 33 returns to convexly protrude outwards, and the pressure in the chamber 34 is relatively lowered compared to the micro-channel 20.

At this time, the movement of the tear from the micro-channel 20 at the downstream side of the chamber 34 is lowered due to the operation of the net one-way valve 23, and the tear is drawn into the chamber 34 from the micro-channel 20 at the upstream side of the chamber 34.

If the wearer repeatedly blinks the eye naturally in a state of wearing the device 1 for collecting tear on the eyeball like a contact lens, the protrusion 33 reciprocates outward and inward by the movement of the eyelid, and a pressure gradient is formed at the entire micro-channel 20 in the outward direction. This pressure difference causes the tear to flow in the outward direction within the micro-channel 20.

As shown in the figures, when a plurality of pumps 30 are provided, the protrusions 33 of the pumps 30 move substantially simultaneously by the eyelid, and help the tear to flow uniformly at the entire micro-channel 20.

According to this configuration, if the wearer just blinks the eye naturally while wearing the device 1 for collecting tear on the eyeball like a contact lens, the tear is introduced into the tear inlet 21 by the pressure generated by the pump 30.

The tear introduced into the tear inlet 21 flows into the storage 40 through the storage entry 41. As a new tear enters the storage entry 41, the tear, which has existed in the storage 40, passes through the storage exit 42, flows along the micro-channel 20, and is discharged to the outside through the tear outlet 22.

As described above, the artificial tear previously filled in the storage 40 and the micro-channel 20 allows the natural tear that is ejected from the eye to be more easily introduced into the micro-channel 20. After a predetermined time, the artificial tear and the tear generated by the stimulation caused by wearing the contact lens are entirely discharged from the storage 40, and the tear discharged from the eye is stored in the storage 40.

After sufficient time, the device 1 for collecting tear may be removed from the eyeball and disassembled or subjected to high pressure to collect undiluted tear. However, the method of separating the tear existing in the storage 40 is not limited thereto.

According to this configuration, while the wearer wears the device 1 for collecting tear, the tear is naturally collected without any additional action, so that it is possible to analyze tear components exactly.

In addition, since the pump driven by the eyelid is used to collect tear, instead of an electronic pump, the structure of the device is simple and the wearer is not burdened to wear the device at all.

Figure 5A:
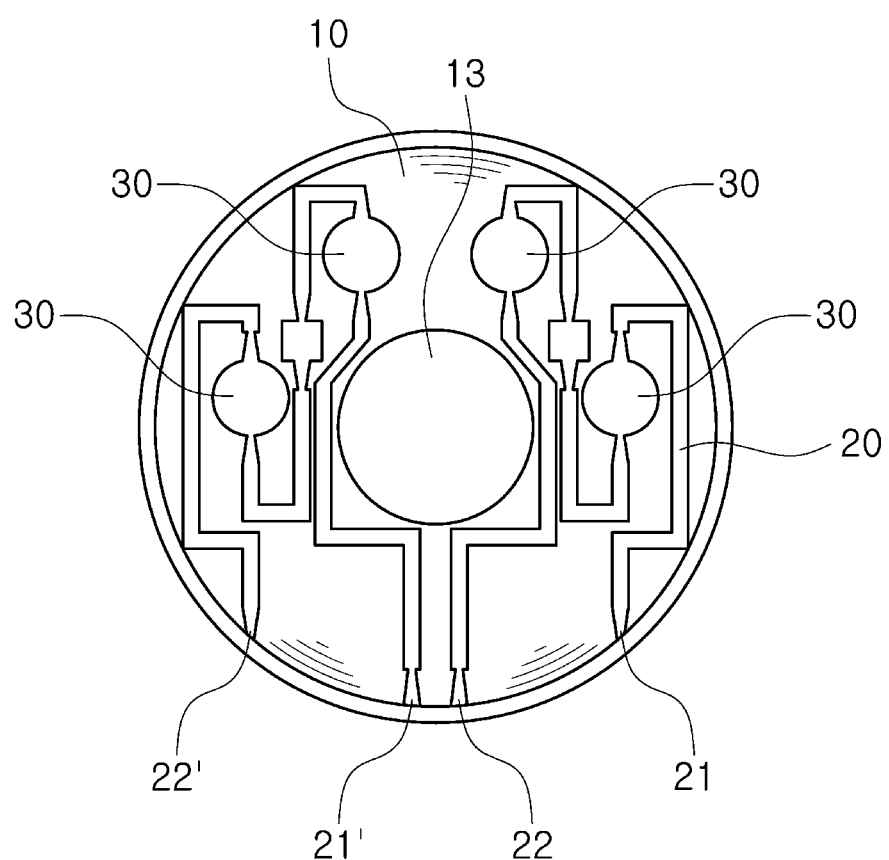
FIG. 5A and FIG. 5B shows a device for collecting tear according to another embodiment of the present disclosure.
Figure 5B:
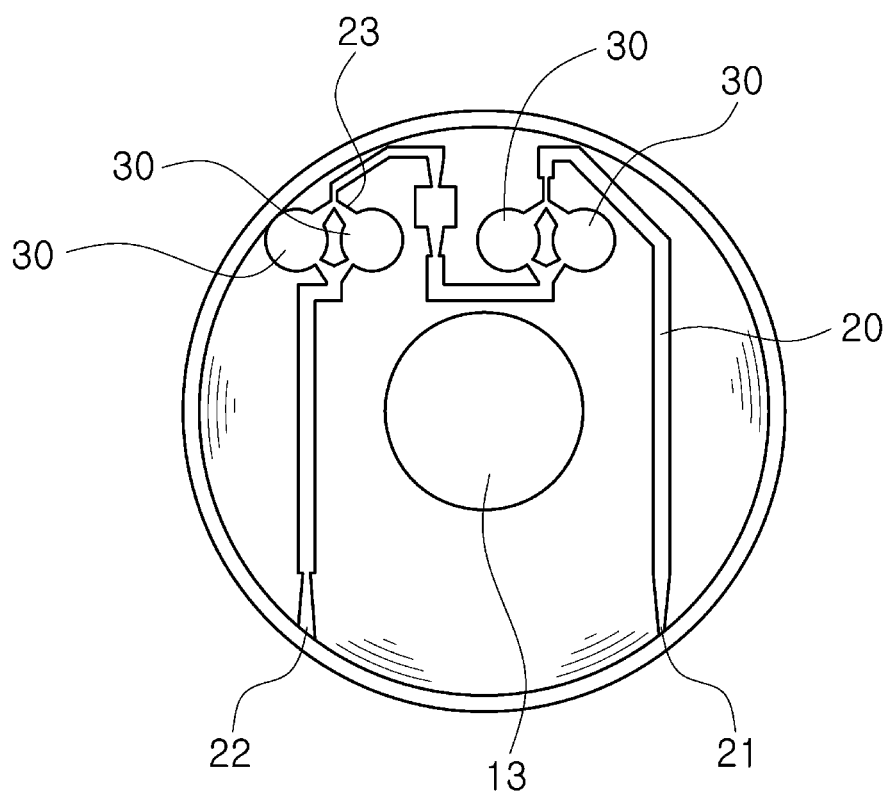

FIG. 5A and FIG. 5B show a device for collecting tear according to another embodiment of the present disclosure.

As shown in FIG. 5A, according to this embodiment, a pupil region 13 in which the pupil of the wearer is located, is formed at a center of the body 10, and the micro-channel 20, the pump 30 and the storage 40 are all formed away from the pupil region 13, so that the eyesight of the wearer is not disturbed while collecting tear. According to this embodiment, the tear inlet 21 and the tear outlet 22 are formed in the same direction.

As shown in FIG. 5A, a plurality of micro-channels 20 respectively having tear inlets 21, 21' and tear outlets 22, 22' may be formed to collect a large amount of tears at a time.

Meanwhile, as shown in FIG. 5B, the micro-channel 20 may include a manifold that is diverged into several branches, and one pump 30 may be formed at each branch of the manifold.

According to this configuration, a pressure gradient is well formed in the micro-channel 20, and thus the flow efficiency of the tear may be increased.

In the above embodiment, the tear is stored in the storage 40, the device 1 for collecting tear is removed from the eyeball, and then the tear is extracted from the storage 40. However, the present disclosure is not limited thereto.

Figure 6:
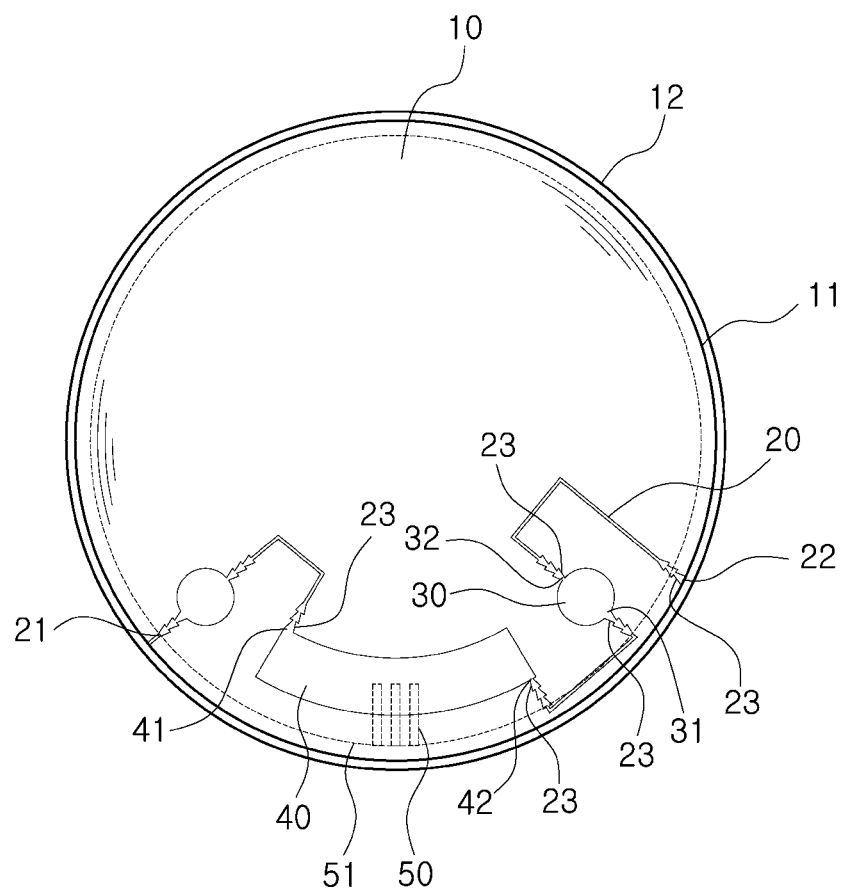
FIG. 6 shows a device for collecting tear according to another embodiment of the present disclosure.

FIG. 6 shows a device for collecting tear according to another embodiment of the present disclosure.

As shown in FIG. 6, a sensor 50 capable of detecting tear components may be provided in the storage 40. The sensor 50 of this embodiment may be a glucose detecting sensor capable of detecting glucose in the tear. However, the sensor 50 is not limited to the detection of glucose, and may be a sensor capable of detecting various components included in the tear.

An electric wire 51 electrically connected to the sensor 50 and capable of transmitting a signal from the sensor 50 may be disposed at the periphery of the body 10.

According to this configuration, the tear components stored in the storage 40 may be detected in real time.

Figure 7:
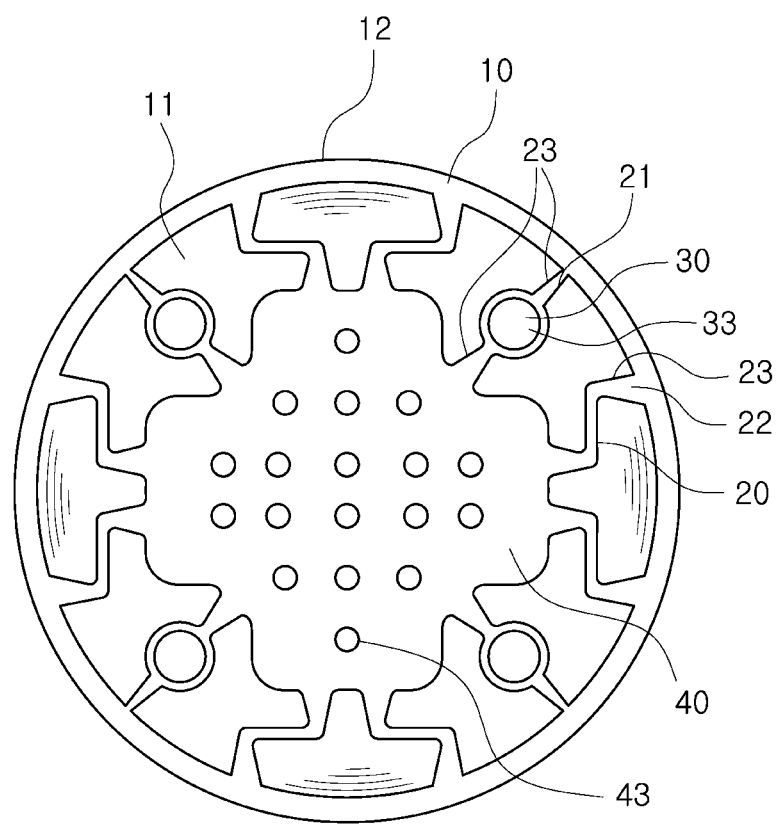
FIG. 7 shows a device for collecting tear according to another embodiment of the present disclosure.

FIG. 7 shows a device 1 for collecting tear according to another embodiment of the present disclosure.

According to this embodiment, the storage 40 is disposed in the center portion of the body 10, and a plurality of tear inlets 21 and tear outlets 22 are formed radially with respect to the center portion of the body 10 in all directions.

According to this configuration, when the device 1 for collecting tear is worn, even if the body 10 rotates within the eyeball, the tear may be smoothly collected regardless of the position of the tear.

Meanwhile, according to this embodiment, since the storage 40 is formed in the center portion, a space for storing a larger amount of tear may be secured.

However, in order to prevent the storage 40, formed in a space between the outer film 11 and the inner film 12, from being compressed by the pressure of the eyelid of the wearer to reduce its volume, according to this embodiment, a plurality of pillar 43 may be formed at the storage 40 to be disposed between the outer film 11 and the inner film 12 to maintain the space.

Figure 8:
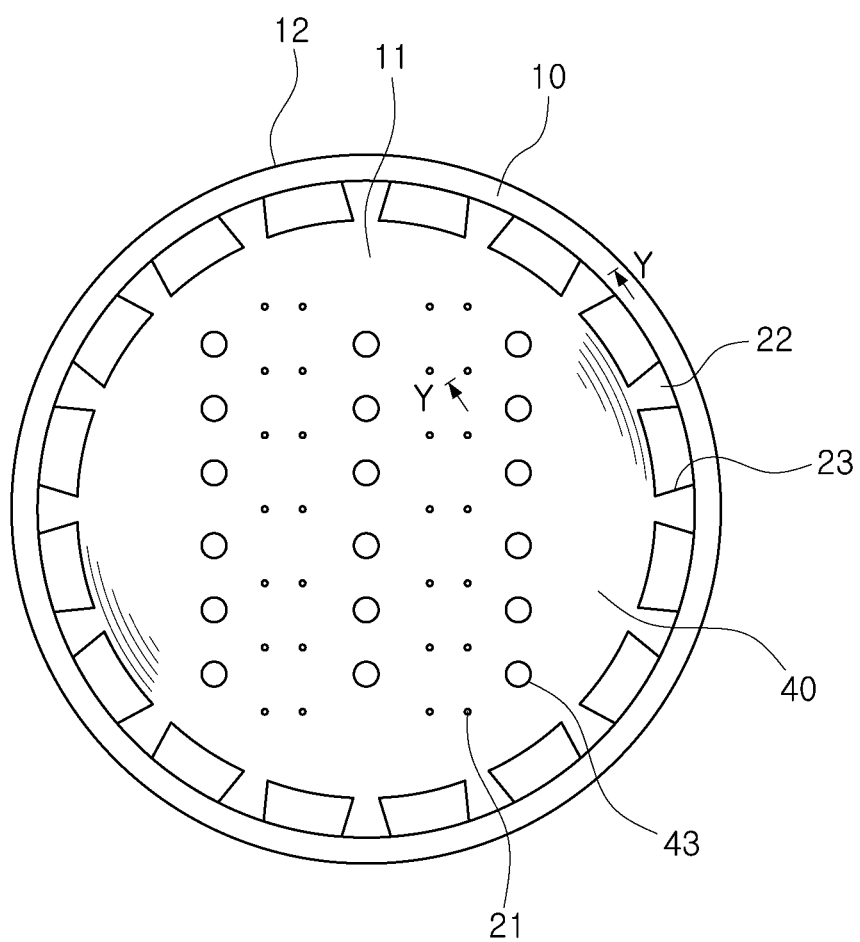
FIG. 8 shows a device for collecting tear according to another embodiment of the present disclosure.
Figure 9:
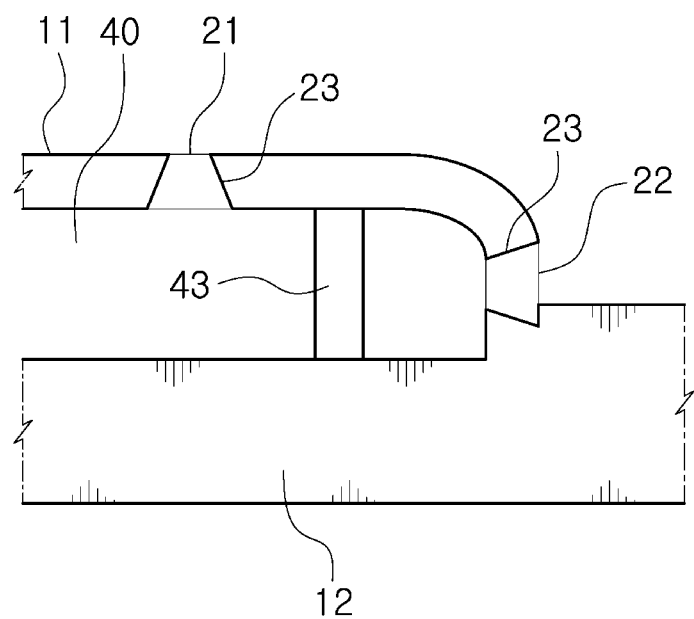
FIG. 9 is a side view, sectioned along the line Y-Y of FIG. 8.

FIG. 8 shows a device for collecting tear according to another embodiment of the present disclosure, and FIG. 9 is a side view, partially sectioned along the line Y-Y of FIG. 8.

As shown in FIGS. 8 and 9, the pump of the device for collecting tear according to this embodiment is composed of a outer film 11 protruding toward the outer of the body 10 and a chamber formed between the outer film 11 and the inner film 12.

Similar to the former embodiment, the outer film 11 is configured to be pressed by the eyelid when the wearer closes the eye and to be returned to its original convex state when the eye is opened. Also, when the wearer blinks the eye, the outer film reciprocates outward and inward to generate a pressure change in the chamber.

According to this embodiment, the storage 40 located at the center portion of the body 10 acts as the chamber of the pump at the same time.

As shown in FIGS. 8 and 9, according to this embodiment, a plurality of tear inlets 21 are opened at the outer surface of the outer film 11, and a net one-way valve 23 is formed adjacent to the tear inlets 21 so that the tear flowing into the tear inlets 21 does not flow inward.

In addition, a plurality of tear outlets 22 are opened toward the side of the outer film 11 and radially arranged.

Meanwhile, the positions of the tear inlets 21 and the tear outlets 22 are not limited to this embodiment, and it is also possible that the tear outlets 22 are opened at the outer surface of the outer film 11 and the tear inlets 21 are opened toward the side of the outer film 11.

According to this embodiment, the tear naturally discharged from the eye is introduced into the storage 40 through the tear inlet 21 by means of the outward and inward reciprocation of the outer film 11, and since the artificial tear filled in the storage 40 may be discharged through the tear outlet 22, the tear naturally discharged from the eye is stored in the storage 40.

According to this embodiment, since the storage may be formed over a very large area between the outer film 11 and the inner film 12, the amount of collected tear may be maximized. In addition, since the pump is constituted by the outer film 11 and the inner film 12, it is not required to separately form a micro-channel, a chamber and a net one-way valve of a complicated configuration.

Meanwhile, according to this embodiment, since the outer film 11 of a relatively large area moves outward and inward, a plurality of pillar 43 for holding a space between the outer film 11 and the inner film 12 at a predetermined level or more may be formed.

The stiffness, intervals and arrangement of the plurality of pillars 43 may be adjusted so that the pillars 43 may prevent the outer film 11 and the inner film 12 from adhering to each other without excessively restraining outward and inward movement of the outer film 11.

What is claimed is:

1. A device for collecting tear fluid, comprising:
a body configured to be placed over an eyeball;
a tear inlet for allowing tear fluid to flow into the body;
a storage formed inside the body and capable of storing the tear fluid having flowed into the body; and
a pump configured to form a pressure difference inside the body from a pressure outside the body such that the tear fluid flows into the body through the tear inlet,
wherein
the pump is driven by using an eye blinking movement of a wearer so as to form the pressure difference inside the body, thereby allowing the tear fluid to flow into the body,
the body is formed with an outer film and an inner film,
the pump includes a protrusion configured to convexly protrude from the outer film outwardly of the body, and
the protrusion is configured to be pressed due to a pressure of the eyelid when the wearer closes the eye and return to an original convex shape when the eye is opened.

2. The device for collecting tear fluid according to claim 1, further comprising:
a tear outlet for allowing the tear fluid to discharge from the body,
wherein the tear fluid circulates by flowing into the body through the tear inlet from an outside of the body and then discharging out of the body through the tear outlet.

3. The device for collecting tear fluid according to claim 2,
wherein a plurality of tear inlets and tear outlets are provided, and
wherein the plurality of tear inlets and tear outlets are radially formed in all directions of the body.

4. The device for collecting tear fluid according to claim 1, further comprising:
a micro-channel configured to extend into the body and communicate with the storage; and
a chamber formed at an inner side of the protrusion between the outer film and the inner film on a path of the micro-channel,
wherein
an entry net one-way valve is formed at an entry side of the chamber and an exit net one-way valve is formed at an exit side of the chamber, the entry net one-way valve including a pump entry having an opening on the entry side of the chamber, and the exit net one-way valve including a pump exit having an opening on the exit side of the chamber,
a sectional area of the entry net one-way valve increases in a direction toward the opening on the entry side of the chamber, and
a sectional area of the exit net one-way valve increases in a direction away from the opening on the exit side of the chamber.

5. The device for collecting tear fluid according to claim 4,
wherein the micro-channel includes a manifold, which is diverged into several branches, in a partial portion thereof, and
wherein one pump is formed at each branch of the manifold.

6. The device for collecting tear fluid according to claim 4,
wherein the exit net one-way valve is formed by changing a width of the micro-channel, and
wherein a width of the exit net one-way valve is gradually increased along a flowing direction of the tear fluid.

7. The device for collecting tear fluid according to claim 6,
wherein a plurality of net one-way valves including the entry one-way valve and the exit one-way valve are adjacently connected in series and are formed at the micro-channel.

8. The device for collecting tear fluid according to claim 1,
wherein the pump further includes:
a chamber formed at an inner side of the protrusion between the outer film and the inner film,
wherein the pressure difference is generated by means of a pressure change inside the chamber, which is generated by outward and inward reciprocating movements of the protrusion when the wearer blinks the eye.

9. The device for collecting tear fluid according to claim 8,
wherein the chamber includes:
a pump entry through which the tear fluid flows into the chamber; and
a pump exit through which the tear fluid discharges from the chamber,
wherein a net one-way valve is provided at the pump entry or the pump exit of the chamber, or at the pump entry and the pump exit of the chamber.

10. The device for collecting tear fluid according to claim 1,
wherein the storage includes:
a storage entry through which the tear fluid flows into the storage; and
a storage exit through which the tear fluid discharges from the storage,
wherein a net one-way valve is provided at the storage entry or the storage exit of the storage, or at the storage entry and the storage exit of the storage.

11. The device for collecting tear fluid according to claim 1,
wherein a plurality of pumps are provided, and
wherein the plurality of pumps are arranged at an upstream side and a downstream side of the storage.

12. The device for collecting tear fluid according to claim 1,
wherein the pump further includes:
a chamber formed between the outer film and the inner film,
wherein the outer film is configured to be pressed due to a pressure of the eyelid when the wearer closes the eye and return to an original convex shape when the eye is opened, and
wherein the pressure difference is generated by means of a pressure change inside the chamber, which is generated by outward and inward reciprocating movements of the outer film when the wearer blinks the eye.

13. The device for collecting tear fluid according to claim 12,
wherein the chamber forms the storage.

14. The device for collecting tear fluid according to claim 12,
wherein the tear inlet is formed at an outer surface of the outer film.

15. The device for collecting tear fluid according to claim 12, further comprising:
a plurality of tear outlets configured to communicate with the inside of the body,
wherein the plurality of tear outlets are radially arranged at a side of the outer film.

16. The device for collecting tear fluid according to claim 1,
wherein the body is in the form of a contact lens.

17. The device for collecting tear fluid according to claim 16,
wherein the body has a pupil region at a center of the body so that the pupil is located in the pupil region, and
wherein the storage is formed away from the pupil region.

18. The device for collecting tear fluid according to claim 16,
wherein the storage is formed at a center portion of the body.

19. The device for collecting tear fluid according to claim 18,
wherein the storage is formed in a space between the outer film and the inner film, and
wherein a pillar is formed at the storage to maintain the space between the outer film and the inner film.

20. The device for collecting tear fluid according to claim 1,
wherein a sensor is formed at the storage to detect components of the tear fluid.

* * * * *